(12) United States Patent
Takai et al.

(10) Patent No.: US 6,417,426 B1
(45) Date of Patent: *Jul. 9, 2002

(54) BODY FLUID ABSORBENT ARTICLE

(75) Inventors: Hisashi Takai; Junichi Noguchi; Hiroki Goda, all of Kagawa-ken (JP)

(73) Assignee: Uni-Charm Corporation, Ehime-Ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/031,820

(22) Filed: Feb. 27, 1998

(30) Foreign Application Priority Data

Feb. 28, 1997 (JP) ............................. 9-061794

(51) Int. Cl.⁷ ............................................... A61F 13/15
(52) U.S. Cl. ................................. 604/378; 604/385.01
(58) Field of Search ................................ 604/378, 383, 604/385.1

(56) References Cited

U.S. PATENT DOCUMENTS

| | | | | |
|---|---|---|---|---|
| 3,046,986 A | * | 7/1962 | Harwood | 604/378 |
| 3,604,422 A | * | 9/1971 | Sabee | 604/385.1 |
| 3,945,386 A | * | 3/1976 | Anczurowski et al. | 604/378 |
| 3,967,623 A | * | 7/1976 | Butterworth et al. | 604/385.1 |
| 4,077,410 A | * | 3/1978 | Butterworth et al. | 604/385.1 |
| 4,321,924 A | * | 3/1982 | Ahr | 604/383 |
| 4,323,069 A | * | 4/1982 | Ahr et al. | 604/383 |
| 4,324,246 A | * | 4/1982 | Mullane et al. | 604/383 |
| 5,061,258 A | * | 10/1991 | Martz | 604/307 |
| 5,648,142 A | * | 7/1997 | Phillips | 604/383 |
| 5,763,044 A | * | 6/1998 | Ahr et al. | 604/378 |
| 5,885,265 A | * | 3/1999 | Osborn, III et al. | 604/385.1 |
| 5,885,268 A | * | 3/1999 | Bien et al. | 604/385.1 |

FOREIGN PATENT DOCUMENTS

| | | |
|---|---|---|
| EP | 0 737 462 | 10/1996 |
| JP | Sho57-17081 | 4/1982 |
| JP | Hei2-193663 | 7/1990 |
| JP | Hei6-78949 | 3/1994 |
| WO | WO95/13773 | 5/1995 |

* cited by examiner

*Primary Examiner*—Dennis Ruhl
(74) *Attorney, Agent, or Firm*—Lowe Hauptman Gilman & Berner, LLP

(57) ABSTRACT

A body absorbent article such as a sanitary napkin including a topsheet having a skin-contactable surface, a skin-noncontactable surface and a plurality of liquid passages extending through the topsheet from the skin-contactable surface to the skin-noncontactable surface, wherein the topsheet comprises a base layer made of a hydrophilic thermoplastic synthetic resin film or nonwoven fabric and formed with the liquid passages and a flocked layer formed on a top surface of the base sheet.

10 Claims, 2 Drawing Sheets

BODY FLUID ABSORBENT ARTICLE

BACKGROUND OF THE INVENTION

This invention relates generally to body fluid absorbent articles and, more particularly to disposable body fluid absorbent articles such as sanitary napkins or menstruation pads for absorptive retention of menstrual discharge, incontinence pads, bed pads, sheets for surgical operation and diapers.

Disposable body fluid absorbent articles such as sanitary napkins or disposable diapers conventionally comprise a liquid-permeable topsheet, a liquid-impermeable backsheet and a liquid-absorbent core disposed between these sheets. It is well known, for example, in Japanese Patent Application Publication (Kokoku) No. Sho57-17081 and Japanese Patent Application Laid-Open (Kokai) Nos. Hei2-193663 and Hei6-78949 to form the topsheet by a nonwoven fabric or a synthetic resin film having a plurality of openings or capillaries for passage of body fluids or a sheet having similar openings or capillaries and consisting of a synthetic resin film and nonwoven fabric laminated integrally laminated upon a surface of the synthetic resin film.

The topsheet of the aforementioned prior art has achieved certain positive effects but has also experienced problems as follows: For example: in the case topsheet of a nonwoven fabric, body fluids may remain in the topsheet and create discomfort, or spread along a surface of the topsheet under the capillary effect of the fibers (depending, on fiber orientation) and cause a leakage of body fluids. If the topsheet is made of a synthetic resin sheet, the gloss, sliminess and chilliness (coldness) peculiar to synthetic resin often gives the wearer an uncomfortable touch. In addition, the topsheet made of such material tends to contact the wearer's skin too closely to leave a space between the skin and the topsheet required to maintain a desired breathability. Finally, in the case of a topsheet made of the sheet consisting of synthetic resin film and nonwoven fabric sheet laminated integrally upon the surface of the film, such laminated sheet is liable to become rather rigid and expensive.

SUMMARY OF THE INVENTION

In view of the problems as have been described above, it is a principal object of the invention to provide body fluid absorbent articles improved to minimize the previously mentioned problems and to allow body fluids discharged thereon to be rapidly transferred into the article.

The object set forth above is achieved, according to the invention, by a body fluid absorbent article including a topsheet having a skin-contactable surface, a skin-noncontactable surface opposed to the skin-contactable surface and a plurality of liquid passages extending through the topsheet from the skin-contactable surface to the skin-noncontactable surface and arranged to be spaced apart one from another in a direction along planes defined by the skin-contactable and skin-noncontactable surfaces, respectively. The topsheet comprises a base layer and a flocked layer laminated integrally with a top surface of the base layer to form the skin-contactable surface.

According to another embodiment of the invention, the absorbent article further comprises a liquid-absorbent/diffusive sheet provided on the skin-noncontactable surface of the topsheet. The liquid-absorbent/diffusive sheet comprises a hydrophilic second base layer made of a nonwoven fabric and a hydrophilic second flocked layer laminated integrally with a top surface of the second base layer made of a nonwoven fabric to form the skin-noncontactable surface.

DESCRIPTION OF THE PREFERRED EMBODIMENTS

Details of a body fluid absorbent article according to the invention will be more fully understood from the description of a sanitary napkin or menstruation pad as a specific embodiment of the invention given hereunder in reference with the accompanying drawings.

Figure 1:
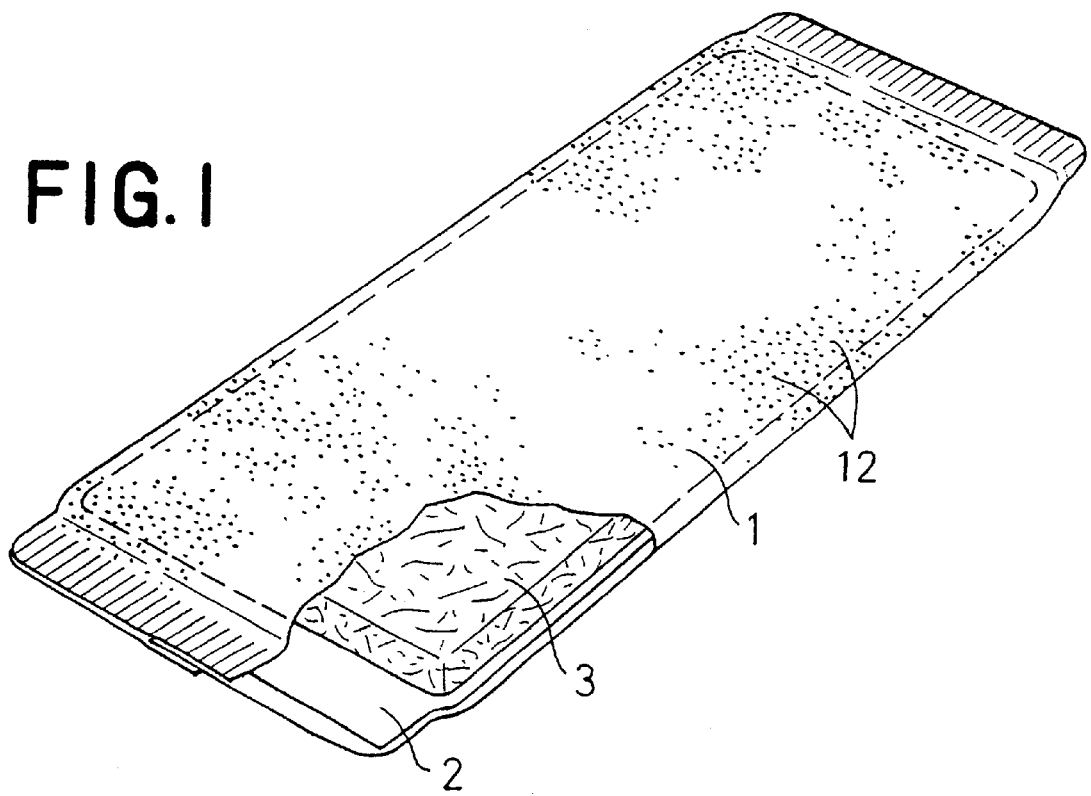
FIG. 1 is a perspective view of a sanitary napkin or menstruation pad as a specific embodiment of the invention as viewed from above a skin-contactable surface thereof.

FIG. 1 is a perspective view showing of a sanitary napkin or menstruation pad as viewed from above a skin-contactable side thereof. The sanitary napkin basically comprises a liquid-permeable topsheet 1, a liquid-impermeable backsheet 2 and a liquid-absorbent core 3 disposed therebetween. The topsheet 1 entirely covers the backsheet 2 as well as the absorbent core 3 and is sealed along longitudinally opposite ends of the sanitary napkin so as to hold the form thereof as the sanitary napkin.

Figure 2:
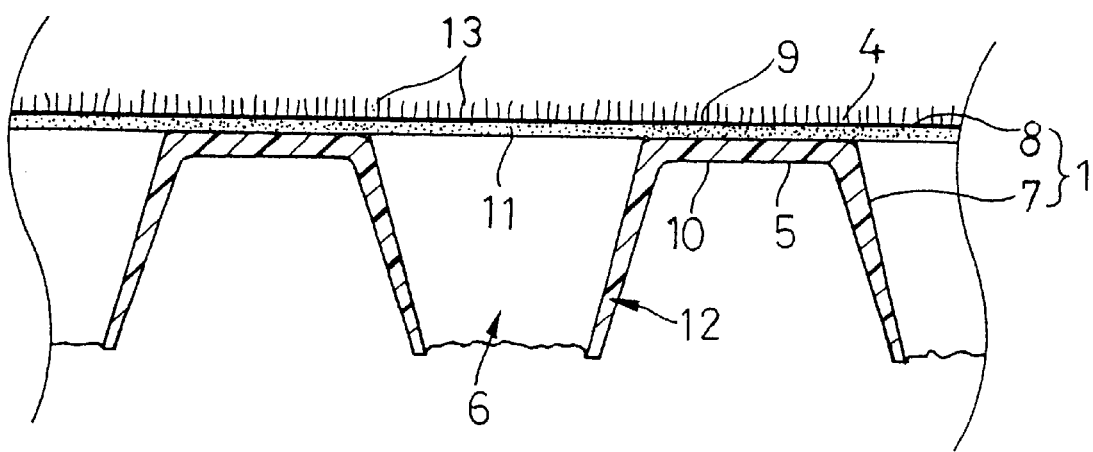
FIG. 2 is a scale-enlarged sectional view schematically and partially showing an embodiment of a topsheet forming part of the sanitary napkin.

Referring to FIG. 2, the topsheet 1 has a skin-contactable surface 4, a skin-noncontactable surface 5 opposed to the skin-contactable surface and a plurality of liquid passages 6. More specifically, the topsheet 1 comprises a base layer 7 and a flocked layer 8. The base layer 7 has the plurality of the liquid passages 6 each extending through the base layer 7 between top and bottom surfaces 9, 10 thereof and being arranged along the surfaces 9, 10 to be spaced apart from the adjacent liquid passages by a given distance. The flocked layer 8 is laminated integrally with the top surface 9 of the base layer 7 by means of an adhesive layer 11 applied on the top surface 9 so as to define the skin-contactable surface 4.

The base layer 7 is made of a thermoplastic resin film. While the thermoplastic synthetic resin film is preferably a low density polyolefine film such polyethylene or polypropylene from the viewpoint of the manufacturing cost, a film of an other type may be also used, for example, polyester, polyamide, EVA or nylon. The film may have a thickness of 7~30$\mu$.

The thermoplastic resin film employed as the base layer 7 may be replaced by a nonwoven fabric of thermoplastic synthetic fibers. The nonwoven fabric may be a melt blown, spun laced, needle punched, thermally bonded, spun bonded or chemically bonded nonwoven fabric of fibers obtained from the previously mentioned synthetic resin. The nonwoven fabric sheet generally has a basic weight of 10~35 g/m$^2$, a density of 0.15~1.25 g/cm$^3$ and a fineness of 0.3~10 d. It should be understood that the fibers may also be conjugate fibers of a core/sheath type consisting of a low melting point resin component and a high melting point resin component.

Both the synthetic resin film and the nonwoven fabric preferably present hydrophilicity from the viewpoint of rapid transfer of body fluids. To achieve this, the synthetic resin as the starting material of the synthetic resin film and the nonwoven fabric preferably contain a suitable hydrophilicity enhancing agent or wetting agent well known in the art. Otherwise, the film or the fabric or the fibers is preferably applied on a surface thereof with the hydrophilicity enhancing agent or wetting agent. These agents may be, in addition to polyethylene glycol well known as surfactant, suitable resins such as CMC or PVA.

The liquid passages 6 are preferably provided in the form of tapered capillaries 12 extending from the bottom surface 10, as shown. To ensure that body fluids can be rapidly transferred into the absorbent core 3 under the capillary effect, the capillaries 12 are distributed at a density of 5~150 capillaries/cm$^2$ and each of these capillaries 12 preferably has a diameter of 0.15~6 mm at a proximal end thereof and a diameter of 0.1~2.5 mm at a distal end thereof. The height of the capillary 12 is preferably limited to 0.05~1.5 mm in order to minimize its deformation, for example, its bending which might often prevent body fluid from being rapidly transferred into the absorbent core 3.

Figure 5A:
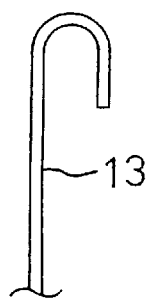
FIGS. 5A and 5B schematic diagrams of examples of in which a distal end of each short fiber (flock, pile) is curved in a flocked layer.
Figure 5B:
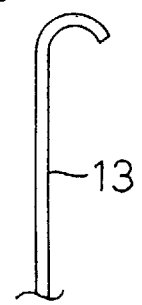

The flocked layer 8 comprises a plurality of hydrophobic short fibers 13 in the form of flocks (piles). The short fibers 13 are planted on the base layer 7 with the adhesive layer 11 so as to be substantially vertical to the top surface 9 of the base layer 7. The short fibers 13 generally have a fiber length of 0.3~1.5 mm, a fineness of 0.3~2 d and a basic weight of 8~15 g/m$^2$. Each of these short fibers 13 is preferably shaped to have a curved end as shown by FIGS. 5(A) and (B). This curved shape can be obtained by pressing heating means against the distal end of the short fiber 13. While not shown, the short fibers 13 may be replaced with beads.

Figure 3:
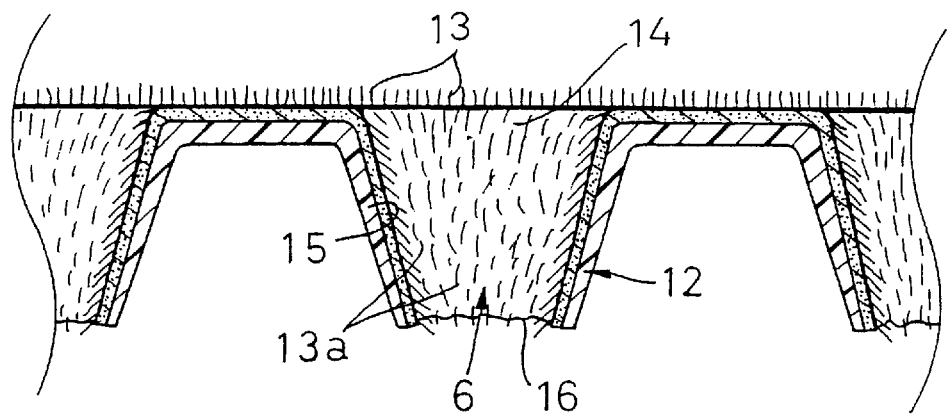
FIG. 3 is a view similar to FIG. 2 showing of another embodiment of the topsheet forming part of the sanitary napkin.

FIG. 3 is a scale-enlarged sectional view schematically and partially showing another embodiment of the topsheet. According to this embodiment, the flocked layer 8 is provided not only on the top surface of the base layer 7, i.e., on surfaces of ribs defining upper openings 14 of the respective liquid passages 6, but also on inner surfaces 15 of the respective liquid passages 6, i.e., of the respective capillaries 12. It should be understood that the short fibers 13a (flocks, piles) on the inner surfaces 15 are hydrophilic and collapsed toward distal ends 16 of the respective capillaries 12. Hydrophilicity of the short fibers 13a can be obtained by using the previously mentioned surfactant or the other as the hydrophilicity enhancing agent or wetting agent.

Figure 4:
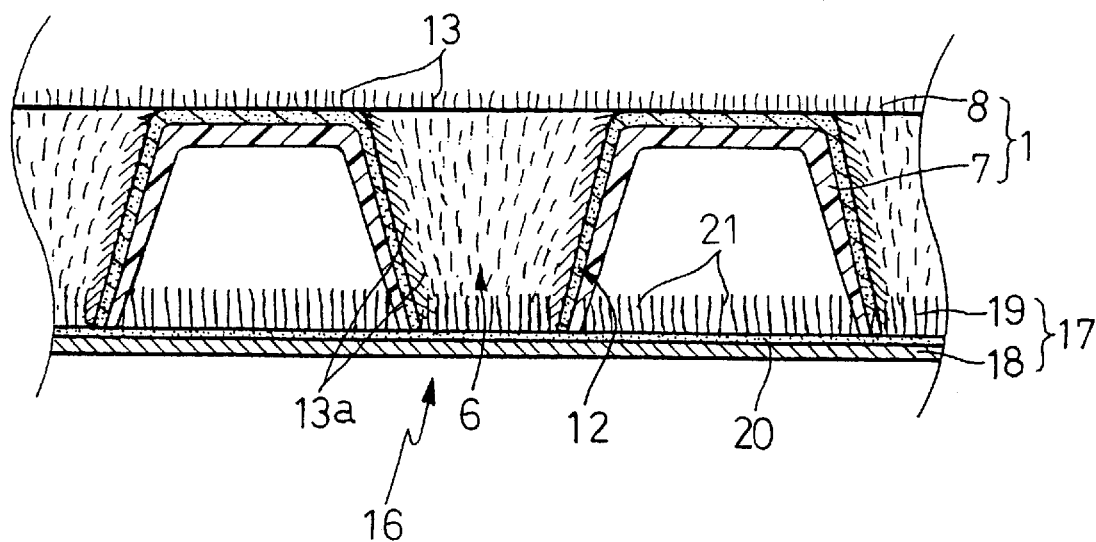
FIG. 4 is a view similar to FIG. 2 showing of still another embodiment of the topsheet and a liquid-absorbent/diffusive sheet combined with the topsheet.

FIG. 4 is a view similar to FIG. 3 of still another embodiment of the topsheet wherein a liquid-absorbent/diffusive sheet 17 is used in combination with the topsheet. Specifically, the liquid-absorbent/diffusive sheet 17 is provided in close contact with the distal ends 16 of the respective capillaries 12 extending through the topsheet 1. This liquid-absorbent/diffusive sheet 17 comprises a base layer 18 made of a hydrophilic nonwoven fabric and a hydrophilic flocked layer 19 laminated integrally with a top surface of the base layer 18. The base layer 18 is substantially similar to the base layer 7 both in its material and its form. More specifically, the base layer 18 is made of thermoplastic fibers provided in the form of a sheet. The flocked layer 19 is similar to the previously mentioned flocked layer 8 so far as the flocked layer 19 comprises hydrophilic short fibers (flocks, piles) planted on the top surface of the base layer 18 made of a nonwoven fabric by an adhesive layer 20 so as to extend vertically from the top surface. The flocked layer 19 is different from the flocked layer 8 only in that each of these short fibers 21 forming the flocked layer 19 has a fiber length larger than that of each short fiber in the flocked layer 8. It is desirable for the base layer 18 made of nonwoven fabric to have a hydrophilicity considerably higher than the hydrophilicity of the nonwoven fabric forming the base layer 7 in order that body fluids may be absorbed by the absorbent core 3 over as large a region as possible.

Although not shown, the topsheet 1 and the liquid-absorbent/diffusive sheet 17 are preferably heat-sealed together intermittently along planes defined by these two sheets 1, 17 by pin embossing under a heating effect.

The flocked layers 8, 19 can be formed by a well-known process and apparatus, for example, the electrostatic flocking process and the apparatus for implementing this process. The adhesive layers 11, 20 to be used for the flocking process may be, for example, selected from various types of silicone resin so far as such resin is adapted for dry cure under irradiation of ultraviolet rays.

The base layer 7 having the liquid passages 6 extending therethrough may be obtained by any one the processes of well known in the art, for example, the processes of the prior art as disclosed in the previously mentioned application. The topsheet 1 according to the specific embodiment shown by FIG. 2 may be made, for example, by forming the base layer 7 with the liquid passages 6 and thereafter by forming such base layer 7 with the flocked layer 8. The topsheet according to the alternative embodiment shown by FIG. 3 may be obtained, for example, by the steps of forming the base layer 7 with the flocked layer 8, and feeding this between a roll provided with a plurality of pyramidal male teeth having pointed and arranged on a peripheral surface thereof and a roll having a plurality of female teeth adapted to be engaged with the corresponding male teeth to form the liquid passages 6 and to collapse the short fibers 13a planted on the inner surfaces of the respective liquid passages 6 in the direction determined by a direction in which the male teeth act on the short fibers. Simultaneously, a suitable hydrophilicity enhancing agent well known in the art previously applied on the male teeth may be transferred to the short fibers 13a planted on the inner surfaces of the respective capillaries 12.

With the body fluid absorbent article according to the invention, the flocked layer laminated with the skin-contactable surface of the topsheet improves appearance, touch and breathability between the skin-contactable surface and a wearer's skin. In addition, the flocks (piles) planted on the skin-contactable surface and extending from the skin-contactable surface substantially in a vertical direction effectively prevent body fluids discharged on the skin-contactable surface from undesirably spreading along this surface and eventually leaking beyond outer peripheral edges of the article. Furthermore, the liquid passages having appropriate hydrophilicity enables body fluids to be rapidly introduced from the skin-contactable surface into the liquid passages and then enables such body fluids introduced into the liquid passages to be rapidly absorbed by the article.

With the liquid passages having the flocks (piles) collapsed toward the distal ends of the respective liquid passages, the transfer of body fluid is promoted. The liquid passages comprising capillaries obviously further promote the transfer of body fluid.

The topsheet provided on its bottom surface with the liquid-absorbent/diffusive sheet further facilitates the body fluid to be rapidly absorbed by the article.

The topsheet laminated integrally with the liquid-absorbent/diffusive sheet advantageously prevents the liquid passages in the form of the capillaries from being undesirably deformed and eliminates a concern that such undesirable deformation might obstruct rapid absorption of body fluid.

What is claimed is:

1. In a body fluid absorbent article including a topsheet having a skin-contactable surface, a skin-noncontactable surface opposed to the skin-contactable surface and a plurality of liquid passages extending through the topsheet from the skin-contactable surface to the skin-noncontactable surface and arranged to be spaced apart one from another, the improvement comprising said topsheet including a base layer and a flocked layer laminated integrally with a top surface of the base layer so as to form the skin-contactable surface, wherein the flocked layer is also provided on inner surfaces of the respective liquid passages.

2. In the absorbent article according to claim 9, wherein short fibers forming the flocked layer on the inner surfaces of the respective liquid passages have a hydrophilicity.

3. In the absorbent article according to claim 2, wherein the short fibers forming the flocked layer on the inner surfaces of the respective liquid passages are collapsed toward distal ends of the respective liquid passages.

4. In a body fluid absorbent article including a topsheet having a skin-contactable surface, a skin-noncontactable surface opposed to the skin-contactable surface and a plurality of liquid passages extending through the topsheet from the skin-contactable surface to the skin-noncontactable surface and arranged to be spaced apart one from another, the improvement comprising:

said skin-contactable surface including a base layer and a flocked layer laminated integrally with a top surface of the base layer, using a separately applied adhesive material layer therebetween; and said skin-noncontactable surface including a liquid-absorbent/diffusive sheet formed by integrally laminating a hydrophilic second flocked layer with a top surface of a hydrophilic second base layer made of a nonwoven fabric.

5. In the absorbent article according to claim 4, wherein short fibers forming the second flocked layer have a fiber length larger than a fiber length of short fibers forming the flocked layer of the topsheet.

6. In the absorbent article according to claim 4, wherein the second base layer made of nonwoven fabric contains thermoplastic fibers.

7. In the absorbent article according to claim 4, wherein short fibers forming the second flocked layer have a hydrophilicity.

8. In the absorbent article according to claim 4, wherein the liquid passages form capillaries extending beyond the skin-noncontactable surface.

9. In a body fluid absorbent article including a topsheet having a skin-contactable surface, a skin-noncontactable surface opposed to the skin-contactable surface and a plurality of liquid passages extending through the topsheet from the skin-contactable surface to the skin-noncontactable surface and arranged to be spaced apart one from another, the improvement comprising:

said skin-contactable surface including an outer sheet formed by integrally laminating a flocked layer with a top surface of a base layer, using a separately applied adhesive material layer therebetween; and said skin-noncontactable surface including an inner liquid-absorbent/diffusive sheet formed by integrally laminating a hydrophilic second flocked layer with a top surface of a hydrophilic second base layer made of a nonwoven fabric;

wherein the second base layer made of nonwoven fabric contains thermoplastic fibers; and wherein the outer and inner sheets are heat-sealed together intermittently in a direction along planes defined by these two sheets.

10. In a body fluid absorbent article including a topsheet having a skin-contactable surface, a skin-noncontactable surface opposed to the skin-contactable surface and a plurality of liquid passages extending through the topsheet from the skin-contactable surface to the skin-noncontactable surface and arranged to be spaced apart one from another, the improvement comprising said topsheet including a base layer and a flocked layer laminated integrally with a top surface of the base layer, using an adhesive layer therebetween, so as to form the skin-contactable surface, wherein the flocked layer includes short fibers having curved distal ends.

* * * * *